Figure 1:
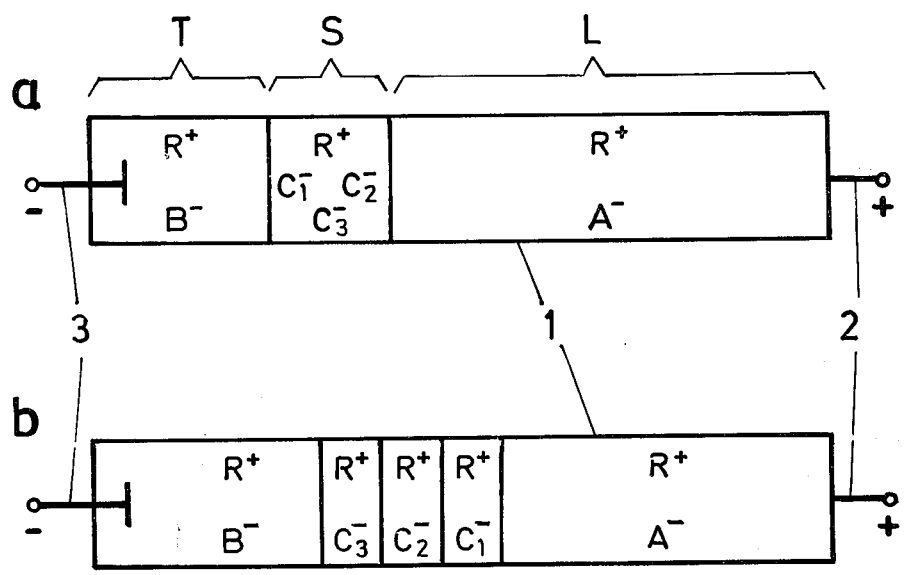

United States Patent [19] [11] 3,948,753
Arlinger [45] Apr. 6, 1976

[54] APPARATUS FOR ISOTACHOPHORETICAL SEPARATION
[75] Inventor: Tord Lennart Arlinger, Ekero, Sweden
[73] Assignee: LKB-Produkter AB, Bromma, Sweden
[22] Filed: Nov. 13, 1974
[21] Appl. No.: 523,498

[30] Foreign Application Priority Data
Nov. 13, 1973 Sweden............................ 7315417

[52] U.S. Cl. ......................... 204/299 R; 204/180 R
[51] Int. Cl.² ........................................... B01K 5/00
[58] Field of Search ................ 204/299, 180 R, 1 T

[56] References Cited
UNITED STATES PATENTS
3,616,456 10/1971 Valmet ............................... 204/299
3,649,499 3/1972 Virtanen et al. ................. 204/180 R
3,869,365 3/1975 Sunden .......................... 204/180 R Primary Examiner—John H. Mack
Assistant Examiner—A. C. Prescott

[57] ABSTRACT
Apparatus for isotachophoretical separation consists of a capillary tube communicating with the sampling zone of a separating column between the leading and terminating electrolytes which are maintained at different electrical potentials.

4 Claims, 3 Drawing Figures

APPARATUS FOR ISOTACHOPHORETICAL SEPARATION

The present invention relates to an apparatus for isotachophoretical separation, comprising a capillary column arranged between two electrodes, the sample subject to separation being introduced between a leading and a terminating electrolyte, respectively, a detector for detection of different sample zones being arranged in a position along said column.

In isotachophoresis a separation of an ionized sample containing ions of a certain polarity is carried out in that way that the sample is introduced into a column arranged between two electrodes, a leading electrolyte being introduced into that part of the column which is situated between the sample and the electrode towards which said ions will migrate when a voltage is applied to the electrodes, said leading electrolyte containing ions of the same polarity but with a greater mobility than the sample ions, a terminating electrolyte being introduced into that part of the column which is situated between the sample and the other electrode, said terminating electrolyte containing ions of said polarity but with a lower mobility than the sample ions. All over the column there is also introduced an ion species of the opposite polarity, a so-called counter ion. The counter ion suitably should have buffering properties.

Isotachophoresis is more closely described for instance in Analytica Chimica Acta 38 (1967) pages 233-237, termed "Displacement electrophoresis" and in the U.S. Pat. No. 3,705,845.

In an isotachophoretical separation of ions a great resolution is achieved in the separation and sharp boundaries will be obtained between the zones formed by the ions. The concentration of ions in the different sample zones is dependent on the mobility of each ion, respectively, and as a consequence a particular ion is generally concentrated as compared to its concentration in the initial sample mixture. These specific features of isotachophoresis, which are a consequence of the presence of a leadind and a terminating electrolyte, respectively, as described above, will make isotachophoretical separation very advantageous as compared to zone electrophoresis in general, in which each sample component zone will be broadened and will receive less sharp border lines as the separation is carried on, as a result of diffusion, and where the concentration of each sample component will decrease during the separation. The advantages of isotachophoresis are particularly eminent in a column, consisting of a capillary tube, in which stabilizing media, such as gels, do not need to be used.

In performance of an isotachophoretical separation generally some kind of detector is arranged at the column for detection of the zone boundaries obtained. A purpose of this detection is to judge when sharp zone boundaries have been formed between all sample zones, as an indication of completed separation. Another purpose of such a detection is to guide a counterflow utilized in many cases, in order that the zone boundary between leading electrolyte and sample mixture is kept stationary in the column, as described in the above mentioned patent specification.

Often an electrophoretical separation, for instance an isotachophoretical separation, is carried out for analytical purposes. Then it is of interest to study the different sample zones as present in the column, to the highest possible resolution in separation and detection. Analytical separations are often carried out in smallest possible sample volume. This will permit short separation time. In analytical isotachophoresis a capillary column is suitably utilized as mentioned above. In a capillary column detection to great resolution of sample component zones is relatively simple to obtain by means of for instance a thermal or optical detector arranged at the column.

In other cases the electrophoretical separation is carried out for preparative purpose, when it is desired to collect the different sample zones separately after the separation. In zone electrophoresis in a column the preparative work entails the emptying of the column from its contents after completed separation and disconnecting of the electrode voltage. During emptying then the zones will be further broadened due to diffusion, and the boundaries will be dissharpened, i.e. the resolution of the separation will be decreased. Preparative separations are generally performed on fairly large sample volumes, which will require macro columns and relatively long separation periods. Detection to a fairly good resolution of sample component zones, as these will be at hand in the column after completed separation, could be achieved only to great difficulty, and detection at preparative separations is usually carried out after elution of the sample components, with said decrease of the resolution of the separation. The elution of a macro column is complicated by the presence of the stabilizing media, for instance gel, which has to be utilized at separations in such columns.

Improved resolution in the separation after elution from a macro column could be achieved by means of a column, where the different sample components influenced by the electrical field are migrating to one end of the column and then, still influenced by the electrical field in a proper way are eluted from the column. Such a device is described in the U.S. Pat. 3697406. This device is intended for samples in macro scale.

It is however desirable to separate also very small sample quantities in a preparative way. A device for preparative isotachophoretical separation in micro scale, i.e. utilizing a capillary column, is not known.

The purpose of the present invention is to provide an apparatus by means of which isotachophoretical separation can be performed preparatively in micro scale. By the apparatus according to the invention there are achieved separations exhibiting very great resolution in short separation periods. The separated sample component zones may be detected prior to the elution to a great resolution in the detection.

According to the invention a shunt tube preferably having smaller cross section than the column is bifurcating from the latter one. Preferably the shunt tube is branching off from the column as close as practically possible to that position in which detection is carried out by means of some kind of detector. Furthermore, the apparatus according to the invention exhibits means for providing a flow of leading electrolyte in the direction opposite to that migration direction of the sample zones.

The characteristics of the invention will be obvious from the claims, following the specification.

Figure 2:
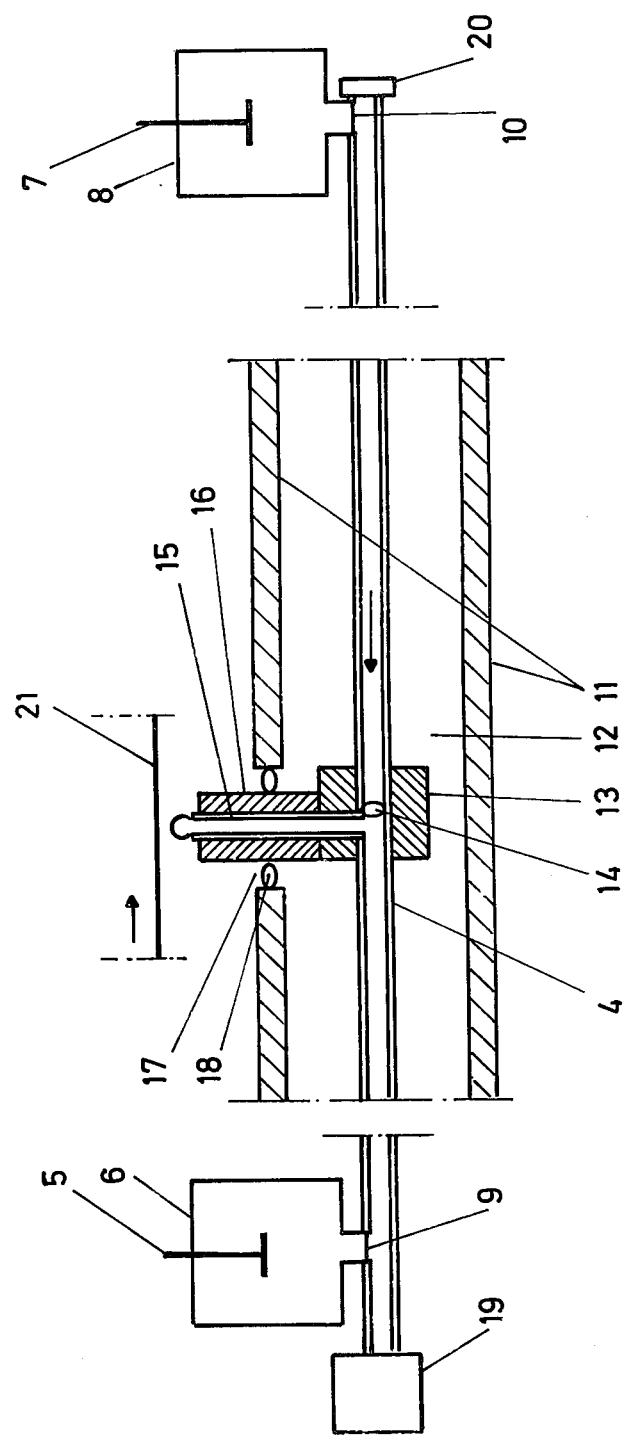

The invention will now be further explained with reference to the attached drawings, on which FIG. 1a and b schematically illustrate the principle of isotachophoresis and FIG. 2 schematically shows a preferred embodiment of the apparatus according to the invention.

In FIG. 1a and 1b the number 1 denotes a column in which an anode 2 and a cathode 3 are introduced. In FIG. 1a the sample to be separated is introduced into that part of the column, denoted by S, and comprises salts having three different anions $C_1^-$, $C_2^-$ and $C_3^-$, of which $C_1^-$ is assumed to have a greater mobility than $C_2^-$, which in its turn is assured to have a greater mobility than $C_3^-$. The part of the column, denoted by L, is filled with the above mentioned leading electrolyte, which consists of the anion $A^-$ having greater mobility than all of the anions of the sample. That part, T, of the column which is turned towards the cathode, is filled with an electrolyte containing an anion $B^-$ having a mobility which is smaller than all the anions of interest in the sample. In L there is a cation species, a so-called counter ion $R^+$ which suitably should have buffering properties. When a direct voltage is applied to the electrodes 2 and 3 the cation species will migrate towards 3 and will constitute a common cation for all anions, while the anions will migrate towards the anode 2. As a consequence of the different mobility of the anions then the electrical field strength over the zones, L, S and T, respectively, will increase stepwise zonewise. This will however bring about that the anions in the zone S will be separated according to their mobility in order than the ions $C_1^-$ which have the greater mobility will form a zone next to the leading electrolyte, followed by a zone consisting of $C_2^-$ and finally a zone consisting of $C_3^-$ next to the terminating electrolyte, see FIG. 1b. Of course, corresponding conditions will be at hand at separation of cations.

In FIG. 2 the number 4 denotes a column consisting of a capillary tube in which the separation is carried out. The number 5 denotes one electrode, which is situated in an electrode vessel 6, filled with leading electrolyte. The migration is assumed to occur in the direction of the arrow, accomplishing separation. The number 7 denotes the other electrode which is contained in an electrode vessel 8 containing terminating electrolyte. That part of the column which is at hand between the sample and the electrode vessel 6 contains leading electrolyte, while that part of the column which is at hand between the sample and the electrode vessel 8 contains terminating electrolyte. The column is delimited towards the electrode vessels by semipermeable membranes 9 and 10, respectively. The electrodes 5 and 7 are connected to a voltage source not shown in the drawing. The number 11 denotes a cooling jacket which forms a cooling channel 12 embracing the column. The cooling channel 12 contains a fluid cooling medium. The number 13 denotes a light path device with a light path 14 transversing the column from a light source, not shown in the drawing, situated on one side of the cooling jacket, to a photometrical detector, likewise not shown in the drawing, situated on the other side of the cooling jacket. In close proximity of the light path there is branched off from the column a shunt tube 15. The shunt tube is mechanically steaded by a cylinder 16 of plexi glass or the like, which is led through the cooling jacket 11 through the opening 17. Between the cooling jacket and the cylinder a sealing 18 is applied. At that part of the column which is at hand between the light path 14 and the electrode vessel 6, a pump 19 is arranged. At that part of the column which is at hand between the detector and the electrolyte vessel 8 a sample injection device 20 is arranged. The number 21 denotes a strip of filter paper which is running over rolls, not shown in the figure, said strip forming a collecting device for the sample components obtained.

In a preparative isotachophoretical separation the sample mixture is introduced into the column at the sample injection device 20, which can be arranged as a septum, which is run through by an injection syringe. As a general rule then leading electrolyte should be introduced into the column between the sample and the membrane 9, terminating electrolyte between the sample and the membrane 10. The outer end of the shunt tube 15 then is closed by a lid, not shown in the drawing. Voltage is applied to the electrodes 5 and 7 and the sample components will migrate isotachophoretically in the direction towards the light path device 13. If the migration distance available is too short, the separation can be accomplished by means of a counterflow, generated by means of the pump 21, according to the above U.S. Pat. No. 3,705,845. Before the sample zones have passed the detector the lid of the shunt tube 15 is lifted off, the pump 19 is started as is the feeding of the strip 21. Immediately after detection the sample component zones are in turn fed out through the shunt tube 15. It is preferred that the shunt tube has a smaller cross section than the column.

The material which is brought out through the shunt tube is collected by a suitable collecting device. According to a preferred embodiment of the apparatus according to the present invention the collecting device comprises a carrier, which at a given rate is conducted past the outer end of the shunt tube, an air gap being at hand between the end of the tube and the carrier. The carrier suitably comprises a strip of a porous material, for instance filter paper, applied to suitable rolls for feeding. As isotachophoretical conditions should be at hand during the feeding out of the sample components, there is applied voltage between the electrodes 5 and 7, which will bring about a potential difference between the carrier in the collecting device and the outer end of the shunt tube. At a certain drop size, depending on potential difference and width of the air gap, the drop formed will make a jump over to the carrier and form a circular spot on this one.

I claim:

1. Apparatus for isotachophoretical separation, comprising a column consisting of a capillary tube and arranged between two electrodes, the sample subject to separation being introduced into said column between leading and terminating electrolytes, respectively, a detector for detection of different sample zones being arranged in a position along the column, characterized in a shunt tube bifurcating from the column in close proximity to the detector position, said shunt tube having smaller cross section than the column and having an open outer end provided with a closable lid, and means for providing a flow of leading electrolyte in the direction towards the sample zones.

2. Apparatus according to claim 1, characterized in a collecting device for sample zones achieved, arranged at the outer end of the shunt tube.

3. Apparatus according to claim 2, characterized in that the collecting device comprises a carrier, which at a certain rate is conducted past the outer end of the shunt tube, an air gap being at hand between the tube end and the carrier, and that an electrical potential is maintained between the tube end and the carrier.

4. Apparatus according to claim 3, characterized in that said carrier consists of a filter paper strip.

* * * * *